US00PP35095P2

(12) United States Plant Patent
Nir

(10) Patent No.: US PP35,095 P2
(45) Date of Patent: Apr. 11, 2023

(54) ***CHAMELAUCIUM* PLANT NAMED 'SIRIUS'**

(50) Latin Name: ***Chamelaucium megalopetalum* x *C. uncinatum***
Varietal Denomination: SIRIUS

(71) Applicant: Nitzan Nir, Kfar Hess (IL)

(72) Inventor: Nitzan Nir, Kfar Hess (IL)

( * ) Notice: Subject to any disclaimer, the term of this patent is extended or adjusted under 35 U.S.C. 154(b) by 0 days.

(21) Appl. No.: 17/849,186

(22) Filed: Jun. 24, 2022

(51) Int. Cl.
*A01H 5/00* (2018.01)
*A01H 6/00* (2018.01)

(52) U.S. Cl.
USPC ..... Plt./229

(58) Field of Classification Search
USPC ..... Plt./229
See application file for complete search history.

*Primary Examiner* — Susan McCormick Ewoldt
(74) *Attorney, Agent, or Firm* — Cassandra Bright

(57) ABSTRACT

A new and distinct *Chamelaucium* cultivar named 'SIRIUS' is disclosed, characterized by abundant, large white flowers and flower buds flushed salmon pink. Petals have a semi-erect attitude. Flower production begins in winter. The new variety is a *Chamelaucium*, normally producing cut flower stems, or as a garden or container plant.

2 Drawing Sheets

Figure 1:
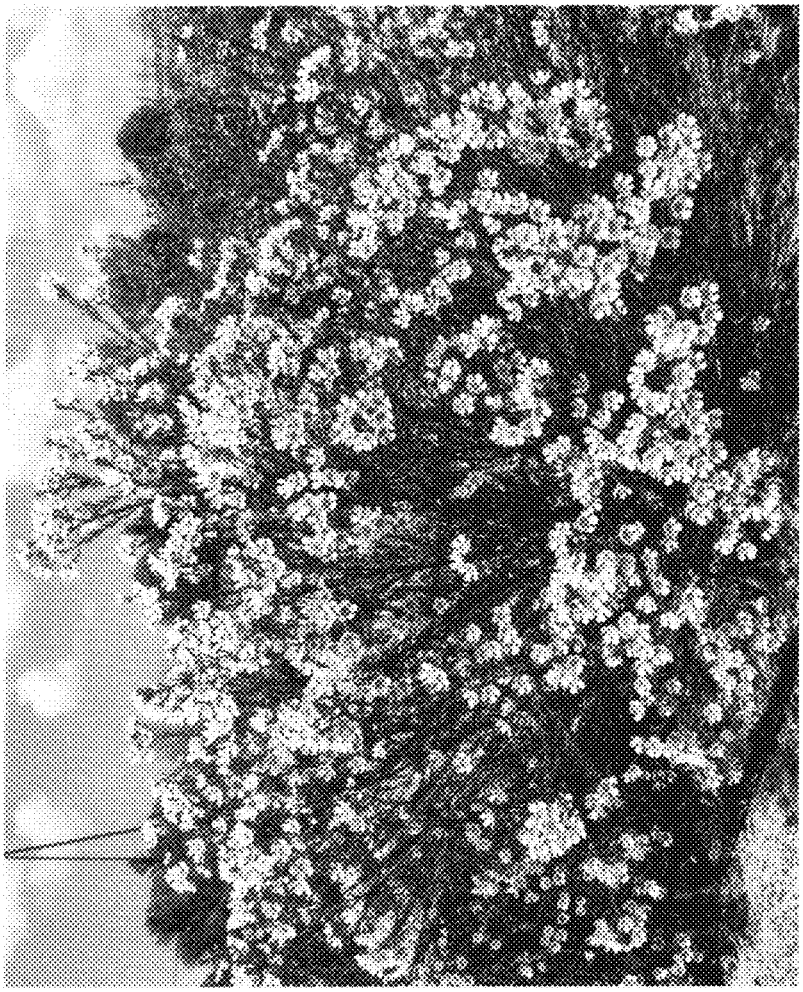

Latin name of the genus and species: *Chamelaucium megalopetalum* x *C. unicinatum.*

Variety denomination: 'SIRIUS'.

BACKGROUND OF THE INVENTION

The new *Chamelaucium* cultivar is the product of a planned breeding program conducted by the inventor, Nitzan Nir, in Kfar Hess, Israel. The objective of the breeding program was to produce new *Chamelaucium* varieties for ornamental commercial applications. The new variety was selected as a seedling from the breeding program at a commercial nursery in Kfar Hess, Israel.

The crossing resulting in this new variety was made in January of 2017. The seed parent is the unpatented variety referred to as *Chamelaucium megalopetalum* 'Guy'. The pollen parent is the unpatented variety referred to as *Chamelaucium uncinatum* 'Atar L'. The new variety was discovered in December of 2019 by the inventor in a group of seedlings resulting from previously mentioned crossing, in a commercial nursery in Kfar Hess, Israel.

Asexual reproduction of the new variety has been performed by terminal vegetative cuttings. This was first performed in May of 2020 at a commercial nursery in Kfar Hess, Israel in and has shown that the unique features of this cultivar are stable and reproduced true to type in at least 4 successive generations.

SUMMARY OF THE INVENTION

The cultivar 'SIRIUS' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SIRIUS'. These characteristics in combination distinguish 'SIRIUS' as a new and distinct *Chamelaucium* cultivar:

1. Large flower size.
2. White flower color.
3. Semi-erect attitude of petals.
4. Large bud size.
5. Salmon pink bud coloration.
6. Upper surface of the receptacle is colored green and maintains this green color.

PARENT COMPARISON

Plants of the new variety 'SIRIUS' are similar to plants of the seed parent in most horticultural characteristics, however, plants of the new variety 'SIRIUS' differ in the following:

1. Upper surface of the new variety's receptacle is green, while that of the seed parent is green when opening, then turns brown when aging.
2. Bud color of the new variety is salmon pink at the apex, and green at the brim. Bud color of the seed parent is red.

Plants of the new variety 'SIRIUS' are similar to plants of the pollen parent in most horticultural characteristics, however, plants of the new variety 'SIRIUS' differ in the following:

1. Bud color of the new variety is salmon pink at the apex, and green at the brim. Bud color of the pollen parent is green.
2. Bud shape of the new variety is flattish, while the bud shape of the pollen parent is round.
3. Buds of the new variety are approximately 30% to 50% larger than buds of the pollen parent.
4. Flowers of the new variety are approximately 30% to 50% larger than flowers of the pollen parent.
5. Petals of the new variety have a semi-erect attitude, while petals of the pollen parent have a horizontal attitude.

COMMERCIAL COMPARISON

Plants of the new variety 'SIRIUS' are comparable to the variety *Chamelaucium uncinatum* 'Adi', unpatented. The two *Chamelaucium* varieties are similar in most horticultural characteristics; however, the new variety 'SIRIUS' differs in the following:

1. Bud color of the new variety is salmon pink at the apex, and green at the brim. Bud color of this comparator is red.
2. Flower color of the new variety is white, while the flower color of this comparator is purple.
3. Upper surface of the new variety's receptacle is green, while that of this comparator is green when opening, then turns brown when aging.

Plants of the new variety 'SIRIUS' are comparable to the variety *Chamelaucium uncinatum* 'Early Maya', unpatented. The two *Chamelaucium* varieties are similar in most horticultural characteristics; however, the new variety 'SIRIUS' differs in the following:

1. Bud color of the new variety is salmon pink at the apex, and green at the brim. Bud color of this comparator is red.
2. Flower size of the new variety is approximately 30% to 50% larger than the flower size of this comparator.
3. Upper surface of the new variety's receptacle is green, while that of this comparator is green when opening, then turns brown when aging.

BRIEF DESCRIPTION OF THE PHOTOGRAPHS

The accompanying photograph in FIG. 1 illustrates a plant of the new variety at approximately 1 to 2 years of age.

Figure 2:
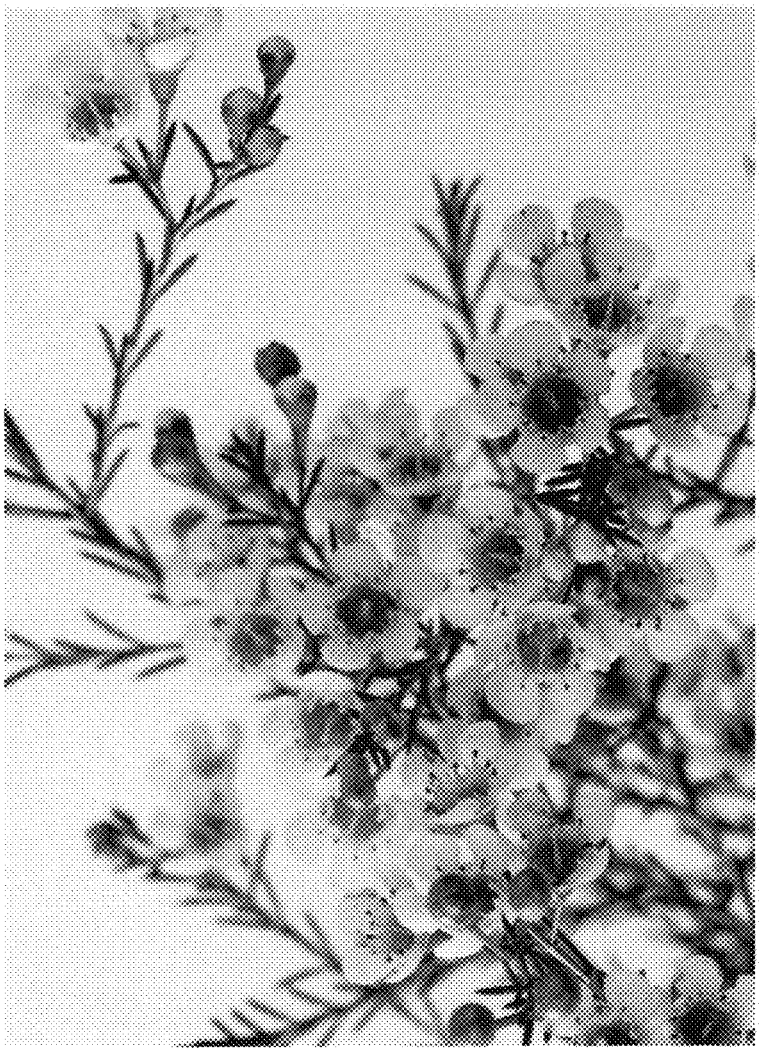

FIG. 2 illustrates a close-up view of the flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'SIRIUS' plants grown outdoors in Kfar Hess, Israel. The growing temperature ranged from 15° C. to 35° C. during the day and from −2° C. to 35° C. during the night. General light conditions are bright, normal sunlight. Measurements and numerical values represent averages of typical plant types.

Botanical classification: *Chamelaucium megalopetalum uncinatum* 'SIRIUS'.

Age of plant described: About 2 months old from a rooted cutting.

Typical flowering stems harvested per plant: 120 to 150 during the course of the season.

Vase life of flowers: Two weeks.

PROPAGATION

Time to produce a rooted plantlet: 30 to 60 days at approximately 24° C.

Root description: Split root.

PLANT

Growth habit: Upright.

Height: 150 cm. to top of foliage; 148 cm. to top of flowers.

Plant spread: 130 cm.

Branching characteristics-

Length of primary lateral branches: 60 cm and up on average.

Diameter of lateral branches: 0.1 to 0.25 cm. (branches from the top 30 cm. of the primary lateral branch).

Quantity of primary lateral branches: 120 to 150.

Characteristics of primary lateral branches:

*Diameter.*—0.4 cm, measured at 50 cm from top.
*Color.*—Near RHS Greyed-Green 197A.
*Texture.*—Smooth.
*Strength.*—Low flexibility.

Internode length: Range from 2 to 8 cm, section of top 30 cm.

FOLIAGE

Leaf:

*Arrangement.*—Opposite.
*Quantity.*—Approximately 10 leaves, in the 5-10 cm section from the top of the branch.
*Average length.*—1.3 cm.
*Average width.*—1.1 mm.
*Shape of blade.*—Needle.
*Apex.*—Acute.
*Base.*—Truncate.
*Margin.*—Entire.
*Texture.*—Smooth.
*Pubescence.*—None.
*Aspect.*—Straight.
*Color.*—Young foliage, upper side: RHS Green 137A. Young foliage, under side: RHS Green 137A. Mature foliage, upper side: RHS Green 137A. Mature foliage, under side: RHS Green 137A.
*Venation.*—Indistinguishable from foliage.
*Petiole.*—Not present.

FLOWER

Natural flowering season: Winter.

Days to flowering from rooted cutting: Photoperiodic conditions. No juvenility.

Inflorescence type: Panicle.

Individual flower type: 5 petals, about 1.8 cm in diameter.

Rate of flower opening: About 45 to 60 days from bud to fully opened flower.

Persistent or self-cleaning: Self-cleaning.

Lastingness: About 2 weeks in a vase.

Bud:

*Shape.*—Flattish.
*Length.*—0.51 cm.
*Diameter.*—0.5 to 0.55 cm.
*Color.*—Near White 155C with strong apical coloration near RHS Red 41B.

Inflorescence size:

*Diameter.*—18 to 24 cm.
*Length.*—22 to 34 cm.

Flower size:

*Diameter.*—1.8 cm.
*Length.*—1.4 cm.

Corolla:

Petals:

*Arrangement.*—Rotate hypanthium.
*Length.*—0.8 cm.
*Diameter.*—0.8 cm.
*Quantity.*—5.
*Texture.*—Smooth.

*Apex*.—Round.
*Base*.—Fused.
*Color*.—When opening: Upper surface: RHS White 155C. Lower surface: RHS White 155C. Fully opened: Upper surface: RHS White 155C. Lower surface: RHS White 155C. Aging: Upper surface: RHS White 155C. Lower surface: RHS White 155C.

Interior corolla/tube:
*Diameter*.—0.9 cm.
*Length*.—0.4 cm.
*Color*.—When opening: Upper surface: RHS Yellow-Green 144A. Lower surface: RHS Yellow-Green 144A. Fully opened: Upper surface: RHS Yellow-Green 144A. Lower surface: RHS Yellow-Green 144A. Aging: Upper surface: RHS Yellow-Green 144A. Lower surface: RHS Yellow-Green 144A.

Calyx/sepals:
*Quantity per flower*.—5 sepals.
*Shape*.—Bow.
*Length*.—0.2 cm.
*Width*.—0.4 cm.
*Margin*.—Smooth.
*Texture*.—Smooth.
*Color*.—RHS White 155C.

Peduncle: Peduncle consists of the plant stem.

Pedicel:
*Length*.—0.6 to 1.3 cm.
*Diameter*.—0.1 cm.
*Color*.—RHS Yellow-Green 146C.

Fragrance: None.

REPRODUCTIVE ORGANS

Stamens:
*Number*.—10.
*Filament length*.—2 mm.
*Filament color*.—Near White 155B.

Anthers:
*Shape*.—Round.
*Length*.—1 mm.
*Width*.—0.3 mm.
*Color*.—RHS Orange 22A.

Pollen: Not observed.

Pistil:
*Number*.—1.
*Length*.—0.75 cm.
*Style length*.—0.7 cm.
*Style color*.—RHS White 155D.
*Stigma*.—Shape: Round. Color: RHS Yellow 18C.

OTHER CHARACTERISTICS

Seeds and fruits: Single flower produces one fruit. When the fruit is fertile, it will produce 1 seed.

Disease/pest resistance: Neither resistance nor susceptibility to the normal diseases and pests of *Chamelaucium* have been observed to date.

Temperature tolerance: From −2° C. to 35° C.

Drought tolerance: Very good tolerance for drought.

What is claimed is:

1. A new and distinct cultivar of *Chamelaucium* plant named 'SIRIUS' as herein illustrated and described.

* * * * *